Nov. 23, 1976 E. E. HETHERINGTON Plant Pat. 3,984
ORCHID
Filed December 22, 1975
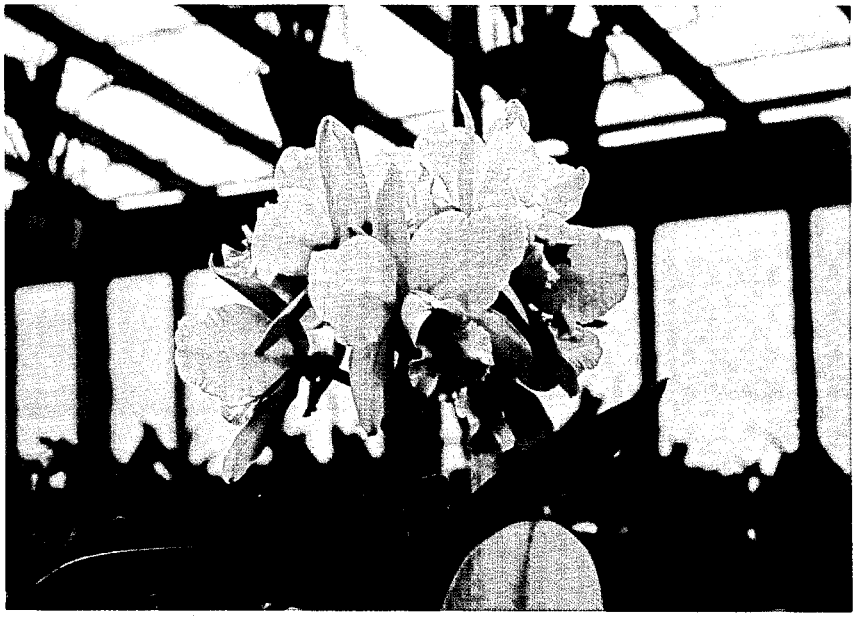
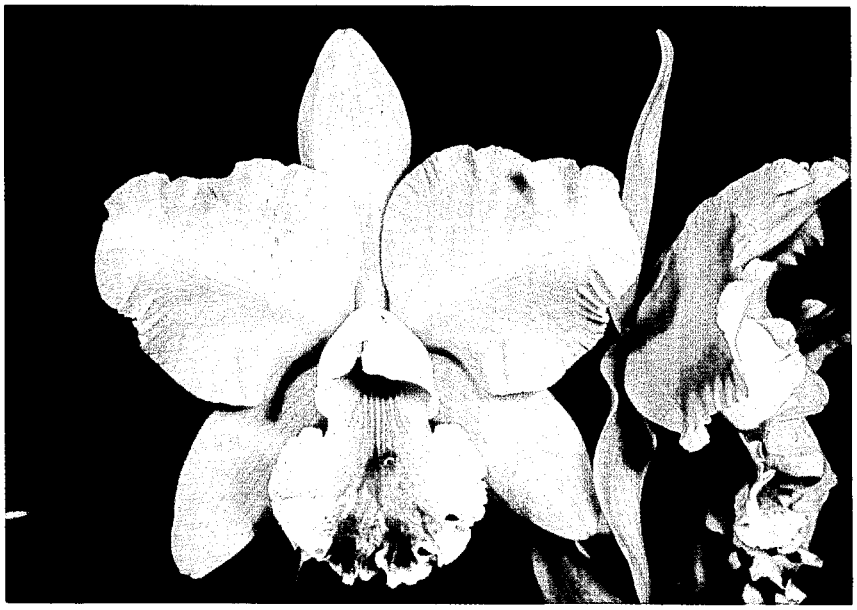

United States Patent

Plant Pat. 3,984

Patented Nov. 23, 1976

3,984

ORCHID

Ernest E. Hetherington, Arcadia, Calif., assignor to Fred A. Stewart Inc., San Gabriel, Calif.

Filed Dec. 22, 1975, Ser. No. 643,071

Int. Cl.[2] A01H 5/00

U.S. Cl. Plt.—68 1 Claim

ABSTRACT OF THE DISCLOSURE

A new and distinct variety of orchid, and more particularly a Brassolaeliocattleya hybrid plant having flowers of a clear green color rare in orchids. The new variety is distinctive from its parents, and from plants of the same hybrid population and from other green flowered orchids, by the unusually large size, greater profusion, longer bloom life, and more enduring fragrance of the flowers, than has been known in other green Cattleya hybrids.

The orchid of this application was discovered by the undersigned discoverer as an outstanding member of a large population of a hybrid Brassolaeliocattleya Memoria Helen Brown (hereinafter Blc. Mem. Helen Brown).

Blc. Mem. Helen Brown had been developed in the orchid nursery of Fred A. Stewart Inc., at San Gabriel, Calif., by crossing Brassolaeliocattleya Xanthette "Chartreuse" (tetraploid) by Laeliocattleya Ann Follis. The Mem. Helen Brown hybrid was registered by Stewart's with the Royal Horticultural Society, London, England, on May 1, 1967, being designated in that registration as "Stewart cross #837, Blc. Mem. Helen Brown." Later, the varietal name "Sweet Afton" was added to identify the individual plant of this application.

After its discovery in 1969, by the applicant herein, the original plant was placed in the laboratories of the Fred A. Stewart Inc. nursery, and during the subsequent years, a large number of plants were asexually reproduced by the meristem method. All of these clones reproduced true to the original plant in both plant and flower, and general characteristics, and all continued to be readily distinguishable from both parentage and the other plants of the same hybrid population.

PLANT PARENTAGE

Brassolaeliocattleya Memoria Helen Brown "Sweet Afton" was developed by crossing Brassolaeliocattleya Xanthette "Chartreuse" (tetraploid) by Laeliocattleya Ann Follis. The Mem. Helen Brown grex was registered by Stewart's on May 1, 1967, Stewart cross #837. The cultivar form "Sweet Afton" was selected from a large population of the grex Mem. Helen Brown for its outstanding quality, in 1969.

DISCOVERY OF THE NEW VARIETY

The discoverer observed a large population of the Cattleya hybrid Mem. Helen Brown, all cultivated in the Stewart's nursery at San Gabriel, Calif. The plant which is the subject of the present application was immediately recognizable as superior in its flowers to all other members of the large population of the hybrid group Mem. Helen Brown. After it had been observed for a period of time, further features of superiority were noted.

ASEXUAL REPRODUCTION

The discoverer has propagated additional stocks of the new Cattleya variety by meristem tissue culture and has accumulated a substantial inventory. A cross section has been flowered. They are exactly the same as the mother clone. The population is carried under Code Number SM-218.

Meristem tissue culture was employed by the discoverer in the Stewart's laboratories to produce a population of the subject plant, by laboratory techniques known as meristem tissue culture. Portions of tissue called meristem, comprised of unspecialized cells, capable of later differentiation, were cut from the plant, and developed, under carefully controlled sterile conditions, into new individual plants. These, in turn, were used as sources of additional portions of meristem tissue.

DESCRIPTION OF THE PLANT

The plant is seen in one of the color photographs accompanying this specification.

Plant growth habit is 37 cm. to 45 cm. on maturity. Leaves are coriacious and 20 to 30 cm. long. (Typical Cattleya strap leaf.) Growth is very strong. The plant's rhizome is short. The growth is compact and erect. Its flowering habit is dependable from developed sheaths. The plants have been virus and pathogen free during the development of this cultivar form for seven years.

The discoverer has conducted microscopic examinations of the cell structure of the plant. The cells have an even chromosome count. The plant is a tetraploid. The Xanthette parent is a known tetraploid.

A self-population of this cultivar variety shows excellent and uniform vigor.

DESCRIPTION OF THE FLOWER

The unusual green flower is seen in the second color photograph accompanying this specification.

Green is one of the most sought after colors in Cattleya hybridizing and one of the most difficult colors to obtain. The task is doubly difficult where larger size, better shape and substance are desired along with the green coloration of the sepals and petals. Most green Cattleyas are small in size, poor of shape and fade too quickly from their opening green color.

The flowers of Blc. Mem. Helen Brown "Sweet Afton," the subject of this specification, are of much larger than average size for green Cattleyas, averaging 15 cm. across the widest span. The petals are flat, well carried without twisting, turning and recurving. The three sepals are in symmetrical balance to the petals and create a good round shape to the flower as a whole. Both sepals and petals (tepals) are uniform light lime green most of the flower life. (British Color Council Horticultural Color Charts, page 663, Chartreuse Green, BCC #171, Intensity #663 to 663-1. Ref. Liquer, Chartreuse.) The texture is sparkling and clear. On full maturity, the flowers become light lemon yellow. (B.C.C.H.C. Charts, p. 4, Lemon, BCC #52, Intensity #4 to 4-1. Ref. Lemon Fruit.)

The rose shaded labellum is semi isthmus (ligulate) with side lobes erectly carried over the column. The column is white.

The Cultivar form "Sweet Afton" can carry up to twelve (12) 6" flowers on a mature well grown plant. Two to four flowers is average for most Cattleyas. The flowers are well carried on a strong erect stem. (See accompanying color photographs.)

The substance of the flowers is very heavy—the flowers lasting for as long as three to four weeks. The green color holds for most of the flower life and changes to light lemon yellow only with full maturity. Unlike most Cattleyas, the sepals do not dry with age but remain firm until the whole flower folds after three to four weeks on the average. Under optimum conditions they last for from four to six weeks.

The blooming season is variable with summer predominating. Twice a year bloom is not rare. The second blooming is generally on the later summer or early winter second growth.

Most Cattleya species and hybrids have their distinctive fragrances. However, in most cases their fragrance is transient and variable depending on the time of the day or night. Mem. Helen Brown "Sweet Afton" is quite extraordinary for its persistent and very strong "rose pepper" fragrance at all times of day or night. The fragrance lasts for the life of the flowers. Practically all Cattleya flowers lose their fragrance shortly after they are cut, but the new cultivar "Sweet Afton" retains fragrance even when cut.

I claim:

1. A new and distinct variety of orchid as described and illustrated, genus Brassolaeliocattleya, an outstanding member of the particular hybrid group described herein, and characterized particularly by its green to yellow flowers which are usually large, profuse, fragant and long-lasting for flowers of its type.

No references cited.

ROBERT E. BAGWILL, Primary Examiner